US012807483B2

(12) United States Patent
Chien et al.

(10) Patent No.: US 12,807,483 B2
(45) Date of Patent: Nov. 24, 2026

(54) SEMICONDUCTOR CHIP WITH EMBEDDED MICROFLUIDIC CHANNELS AND METHOD OF FABRICATING THE SAME

(71) Applicant: National Taiwan University, Taipei (TW)

(72) Inventors: Jun-Chau Chien, Taipei (TW); Wei-Yang Weng, Taipei (TW)

(73) Assignee: National Taiwan University, Taipei (TW)

( * ) Notice: Subject to any disclaimer, the term of this patent is extended or adjusted under 35 U.S.C. 154(b) by 362 days.

(21) Appl. No.: 18/393,670

(22) Filed: Dec. 22, 2023

(65) Prior Publication Data

US 2024/0208806 A1 Jun. 27, 2024

Related U.S. Application Data

(60) Provisional application No. 63/434,889, filed on Dec. 22, 2022.

(51) Int. Cl.

*B81C 1/00* (2006.01)
*B81B 1/00* (2006.01)
(Continued)

(52) U.S. Cl.

CPC .......... *B81C 1/00539* (2013.01); *B81B 1/002* (2013.01); *C12M 23/16* (2013.01); (Continued)

(58) Field of Classification Search

CPC ........ B81C 1/00539; B81C 2201/0142; B81B 1/002; B81B 2201/0214; C12M 23/16; C12M 41/30

See application file for complete search history.

(56) References Cited

U.S. PATENT DOCUMENTS 9,606,081 B2 * 3/2017 Chang ............... B01L 3/502707
10,820,844 B2 11/2020 Scherer et al.
(Continued)

FOREIGN PATENT DOCUMENTS

CN 105977282 9/2016
CN 115497896 12/2022
(Continued)

OTHER PUBLICATIONS

Wei-Yang Weng et al., "CMOS-Embedded 3D Micro/Nanofluidics Employing Topdown BEOL Single-Step Wet-Etching Technique", 2023 IEEE 36th International Conference on Micro Electro Mechanical Systems (MEMS), Jan. 15, 2023, pp. 558-561.
(Continued)

*Primary Examiner* — Fernando L Toledo
*Assistant Examiner* — Jorge Andres Lopez
(74) *Attorney, Agent, or Firm* — JCIPRNET

(57) ABSTRACT

A semiconductor chip with embedded microfluidic channels includes a semiconductor substrate, a circuit structure layer, a first microfluidic channel and a micro via hole. The circuit structure layer includes a first metal layer, a first insulation layer and a second metal layer sequentially disposed on a substrate surface of the semiconductor substrate along a stacking direction. A plurality of first bridge patterns penetrates the first insulation layer, and are each electrically connected to the first metal layer and/or the second metal layer. The first microfluidic channel and the micro via hole are embedded in the circuit structure layer. In the stacking direction, a first height of the first microfluidic channel is equal to a first thickness of the first metal layer. In any direction parallel to the substrate surface, a hole width of the micro via hole is equal to a pattern width of each of the first bridge patterns.

8 Claims, 17 Drawing Sheets

(51) Int. Cl.
*C12M 1/34* (2006.01)
*C12M 3/06* (2006.01)

(52) U.S. Cl.
CPC ..... *C12M 41/30* (2013.01); *B81B 2201/0214* (2013.01); *B81C 2201/0142* (2013.01)

(56) References Cited

U.S. PATENT DOCUMENTS

| | | | | |
|---|---|---|---|---|
| 10,866,229 | B2 | 12/2020 | Meng et al. | |
| 2009/0315126 | A1 | 12/2009 | McAvoy et al. | |
| 2014/0083858 | A1 * | 3/2014 | Teh ...................... | H05K 1/0272<br>204/601 |
| 2020/0350200 | A1 | 11/2020 | Humbert et al. | |

FOREIGN PATENT DOCUMENTS

| | | |
|---|---|---|
| TW | 201022130 | 6/2010 |
| TW | 201726540 | 8/2017 |
| TW | 202143519 | 11/2021 |

OTHER PUBLICATIONS

Wei-Yang Weng et al., "Impedance Sensing in CMOS-Embedded Microfluidics using BEOL Electrodes", Journal of Microelectromechanical Systems, Jan. 1, 2023, pp. 1-7.
"Office Action of Taiwan Counterpart Application", issued on Sep. 4, 2024, p. 1-p. 4.

* cited by examiner

ML3 { CP3, SL1, SL2 }

ML3 { CP3, SL1, SL2 }

SEMICONDUCTOR CHIP WITH EMBEDDED MICROFLUIDIC CHANNELS AND METHOD OF FABRICATING THE SAME

CROSS-REFERENCE TO RELATED APPLICATION

This application claims the priority benefit of U.S. provisional application Ser. No. 63/434,889, filed on Dec. 22, 2022. The entirety of the above-mentioned patent application is hereby incorporated by reference herein and made a part of this specification.

BACKGROUND

Technical Field

This disclosure relates to a microfluidic chip and method of fabricating the same, and in particularly, relates to a semiconductor chip with embedded microfluidic channels and method of fabricating the same.

Description of Related Art

Over the past few decades, many micro/nanofluidic devices for point-of-care (PoC) application have been developed. However, despite miniaturization, most of these devices still require a benchtop instruments to read biosensor signals (such as electrochemical currents, fluorescence, etc.). Therefore, in order to improve the convenience of signal reading, integrating millimeter-level complementary-metal-oxide-semiconductor (CMOS) chips with micro/nanofluidic devices has aroused great interest.

A technology that integrates microfluidics and CMOS components through modular components has been widely studied. However, this type of method usually involves complex manufacturing steps, such as post —CMOS lithography or wafer bonding, which will affect the yield and process time. On the other hand, this type of method will also be limited by the achievable alignment accuracy and reduce the design flexibility of the microfluidic channel.

SUMMARY

The disclosure provides a semiconductor chip with embedded microfluidic channels, which has better cost-efficiency, and the microfluidic structure thereof may have better precision and complexity.

The disclosure provides a method of fabricating a semiconductor chip with embedded microfluidic channels, which is highly integrated with the current semiconductor manufacturing process, and can produce more precise and complex microfluidic structures.

The semiconductor chip with embedded microfluidic channels of the disclosure includes a semiconductor substrate, a circuit structure layer, a first microfluidic channel and a micro via hole. The circuit structure layer includes a first metal layer, a second metal layer, a first insulation layer and a plurality of first bridge patterns. The first metal layer is disposed on a substrate surface of the semiconductor substrate. The second metal layer is disposed on the first metal layer along a stacking direction. The first insulation layer is disposed between the first metal layer and the second metal layer. The first bridge patterns penetrate the first insulation layer and are each electrically connected to at least one of the first metal layer and the second metal layer. The first microfluidic channel is embedded in the circuit structure layer, and located between the second metal layer and the semiconductor substrate. The micro via hole is embedded in the circuit structure layer, and is connected to the first microfluidic channel. An extending direction of the micro via hole intersects the substrate surface of the semiconductor substrate and an extending direction of the first microfluidic channel. A first height of the first microfluidic channel along the stacking direction is equal to a first thickness of the first metal layer along the stacking direction. A hole width of the micro via hole along any direction parallel to the substrate surface is equal to a pattern width of each of the first bridge patterns along the any direction parallel to the substrate surface.

The method of fabricating a semiconductor chip with embedded microfluidic channels of the disclosure includes the following steps: forming a circuit structure layer on a semiconductor substrate by the steps including sequentially forming a first metal layer, a first insulation layer with a plurality of first bridge patterns, a second metal layer on the semiconductor substrate, and performing a wet etching process to remove part of the first metal layer, part of the second metal layer and one of the first bridge patterns. Each of the first bridge patterns is electrically connected to at least one of the first metal layer and the second metal layer. The part of the first metal layer of the circuit structure layer is removed to form a first microfluidic channel. The part of the second metal layer is removed to form a second microfluidic channel. The one of the first bridge patterns is removed to form a micro via hole. The first microfluidic channel is connected to the second microfluidic channel through the micro via hole.

Based on the above, in the semiconductor chip with embedded microfluidic channels and the method of fabricating the same according to an embodiment of the disclosure, a wet etching process can be used to remove part of the metal layers and the bridge patterns formed in the circuit structure layer on the semiconductor substrate to form connected microfluidic channels and micro via holes. Therefore, the microfluidic structure of present disclosure has excellent integration with the semiconductor chip, and the manufacturing cost may be reduced. In addition, the fineness and complexity of microfluidic structures may also be improved by the capabilities of current semiconductor manufacturing process.

To make the aforementioned more comprehensible, several embodiments accompanied with drawings are described in detail as follows.

BRIEF DESCRIPTION OF THE DRAWINGS

The accompanying drawings are included to provide a further understanding of the disclosure, and are incorporated in and constitute a part of this specification. The drawings illustrate exemplary embodiments of the disclosure and, together with the description, serve to explain the principles of the disclosure.

DESCRIPTION OF THE EMBODIMENTS

In the following detailed description of the preferred embodiments, reference is made to the accompanying drawings which form a part hereof, and in which are shown by way of illustration specific embodiments in which the invention may be practiced. In this regard, directional terminology, such as "top," "bottom," "front," "back," etc., is used with reference to the orientation of the Figure(s) being described. The components of the present invention can be positioned in a number of different orientations. As such, the directional terminology is used for purposes of illustration and is in no way limiting. On the other hand, the drawings are only schematic and the sizes of components may be exaggerated for clarity. It is to be understood that other embodiments may be utilized and structural changes may be made without departing from the scope of the present invention. Also, it is to be understood that the phraseology and terminology used herein are for the purpose of description and should not be regarded as limiting. The use of "including." "comprising." or "having" and variations thereof herein is meant to encompass the items listed thereafter and equivalents thereof as well as additional items. Unless limited otherwise, the terms "connected," "coupled," and "mounted" and variations thereof herein are used broadly and encompass direct and indirect connections, couplings, and mountings. Similarly, the terms "facing." "faces" and variations thereof herein are used broadly and encompass direct and indirect facing, and "adjacent to" and variations thereof herein are used broadly and encompass directly and indirectly "adjacent to". Therefore, the description of "A" component facing "B" component herein may contain the situations that "A" component directly faces "B" component or one or more additional components are between "A" component and "B" component. Also, the description of "A" component "adjacent to" "B" component herein may contain the situations that "A" component is directly "adjacent to" "B" component or one or more additional components are between "A" component and "B" component. Accordingly, the drawings and descriptions will be regarded as illustrative in nature and not as restrictive.

Figure 1:
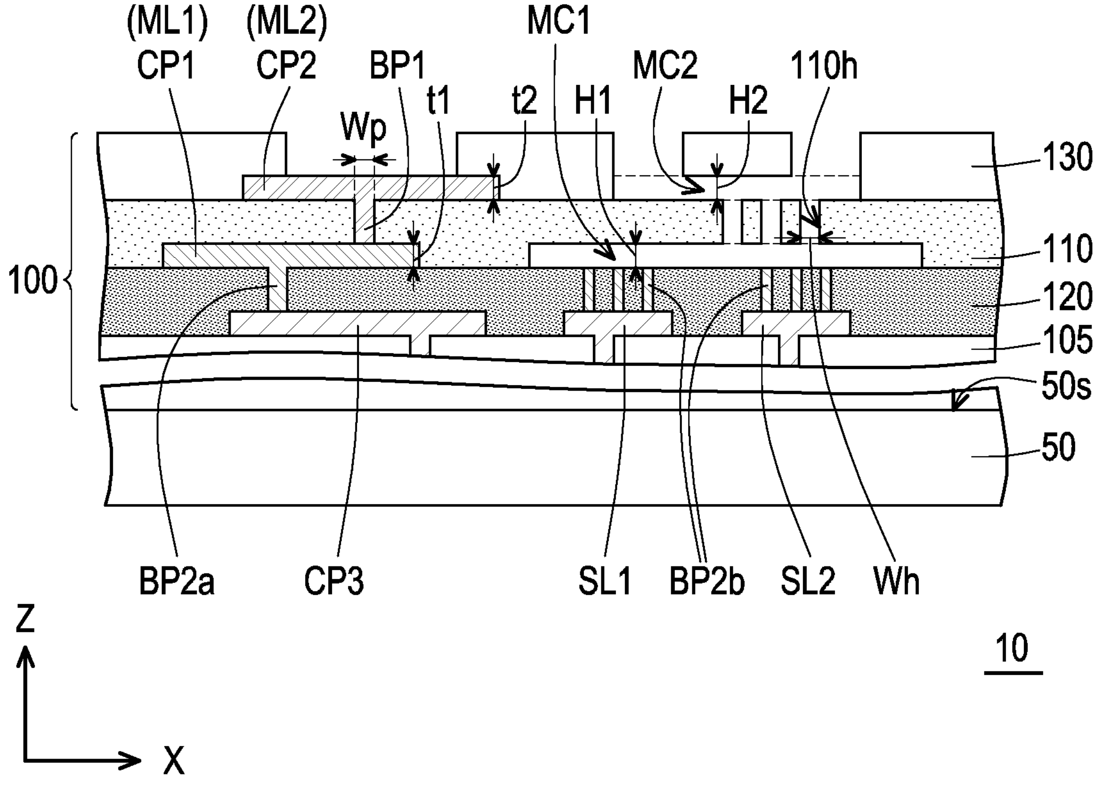
FIG. 1 is a schematic cross-sectional view of a semiconductor chip with embedded microfluidic channels according to a first embodiment of the disclosure.
Figure 3A:
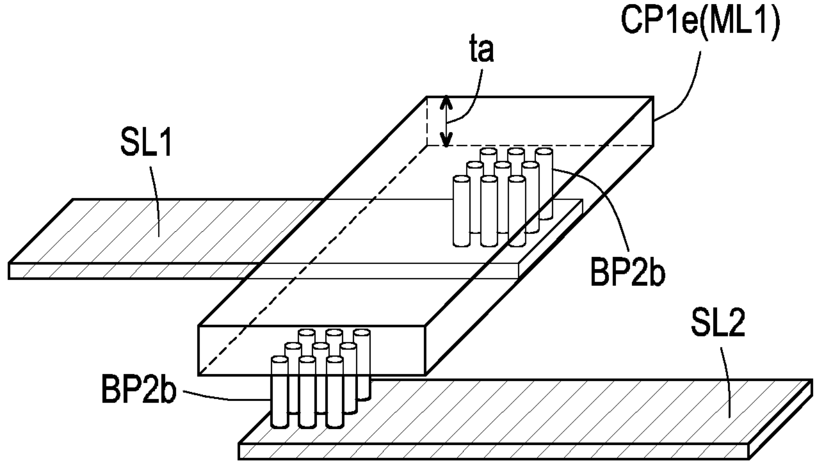
FIG. 3A to FIG. 3C are schematic flow diagrams of the wet etching process of FIG. 2D and FIG. 2E.
Figure 3B:
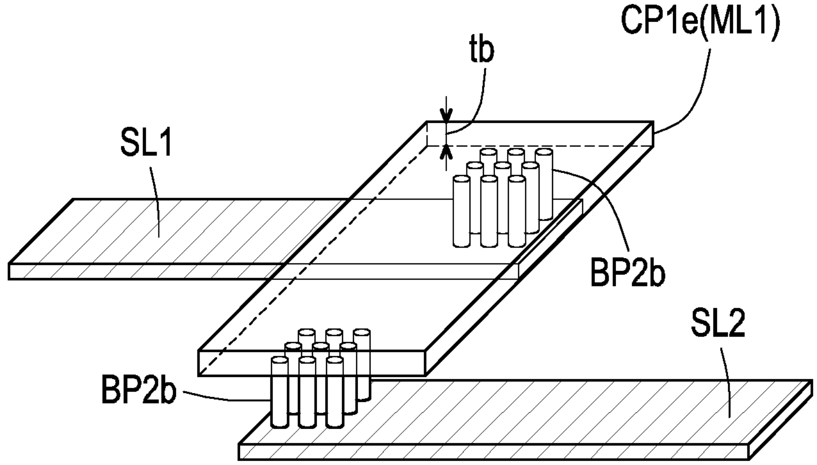
Figure 3C:
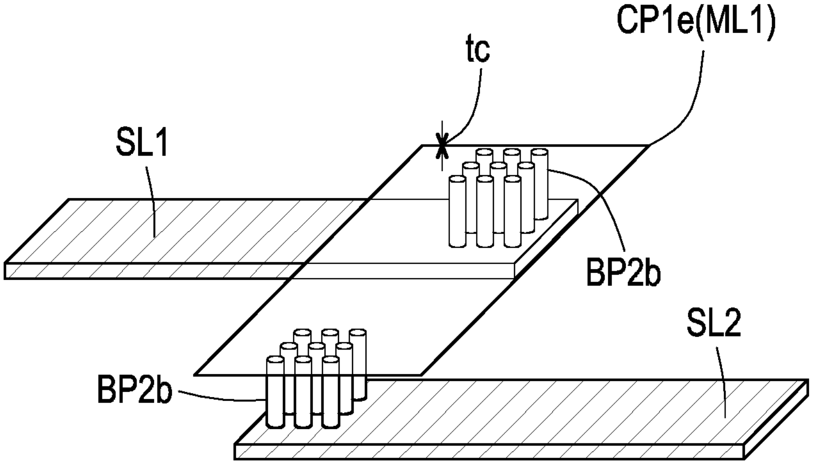
Figure 4:
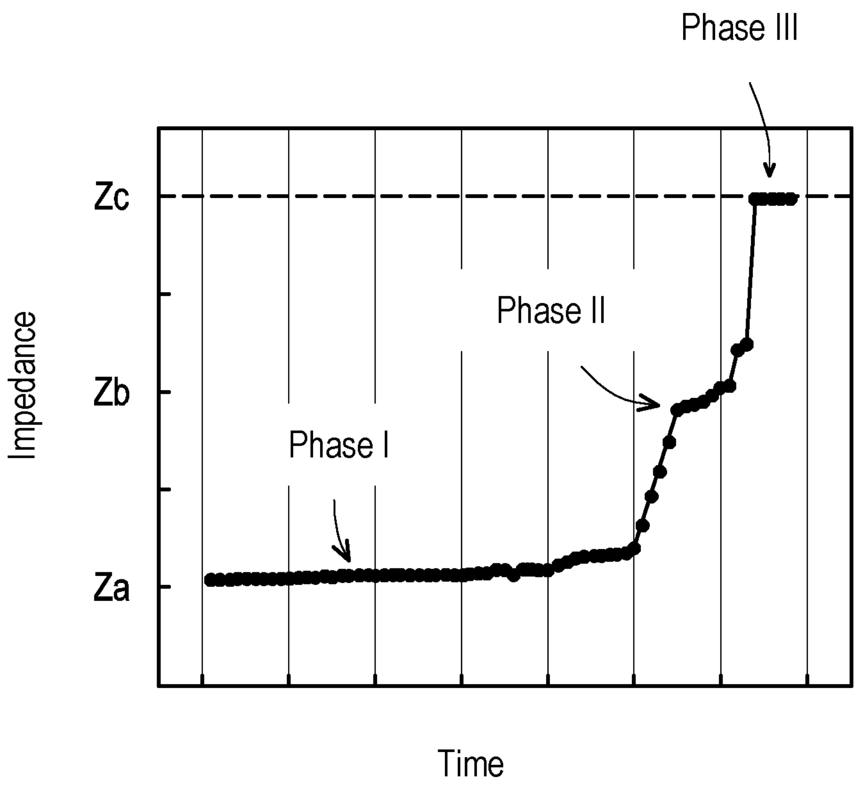
FIG. 4 is a graph showing the impedance of the part of the first metal layer to be removed in the wet etching process in FIG. 2D as a function of time.

FIG. 1 is a schematic cross-sectional view of a semiconductor chip with embedded microfluidic channels according to a first embodiment of the disclosure. FIG. 2A to FIG. 2E are cross-sectional views of a process of fabricating the semiconductor chip with embedded microfluidic channels of FIG. 1. FIG. 3A to FIG. 3C are schematic flow diagrams of the wet etching process of FIG. 2D and FIG. 2E. FIG. 4 is a graph showing the impedance of the part of the first metal layer to be removed in the wet etching process in FIG. 2D as a function of time.

Referring to FIG. 1, a semiconductor chip 10 with embedded microfluidic channels includes a semiconductor substrate 50 and a circuit structure layer 100. The circuit structure layer 100 is provided on a substrate surface 50*s* of the semiconductor substrate 50. In the embodiment, the semiconductor chip 10 with embedded microfluidic channels is, for example, a CMOS chip, and the semiconductor substrate 50 is, for example, a silicon substrate with a plurality of transistors (not shown), but the disclosure is not limited thereto.

The circuit structure layer 100 is formed, for example, in a backend-of-the-line (BEOL) process of a semiconductor chip, and is electrically connected to the transistors on the semiconductor substrate 50. The circuit structure layer 100 may be a three-dimensional circuit structure stacked by a plurality of metal layers, a plurality of insulation layers and a plurality of bridge patterns.

For example, in the embodiment, the circuit structure layer 100 may include a metal layer ML1, an insulation layer 110, a metal layer ML2 and a plurality of bridge patterns BP1. The metal layer ML2 is disposed on the metal layer ML1 along a stacking direction (e.g. direction Z). The insulation layer 110 is disposed between the metal layer ML1 and the metal layer ML2. The bridge patterns BP1 penetrate the insulation layer 110 and are each electrically connected to the metal layer ML1 and the metal layer ML2. That is, the metal layer ML2 is electrically connected to the metal layer ML1 through the bridge patterns BP1.

The semiconductor chip 10 with embedded micro-channels further includes a microfluidic channel MC1, a microfluidic channel MC2 and a plurality of micro via holes 110*h* embedded in the circuit structure layer 100. The microfluidic channel MC1 is located between the metal layer ML2 and the semiconductor substrate 50. The microfluidic channel MC2 is disposed above the microfluidic channel MC1 and is connected with the microfluidic channel MC1 through the micro via holes 110*h*. The extending direction of the micro via holes 110*h* intersects (e.g., is perpendicular to) the substrate surface 50*s* and the extending direction of each of the microfluidic channel MC1 and the microfluidic channel MC2. In the embodiment, the circuit structure layer 100 further includes an insulation layer 130, covering the metal layer ML2 and the insulation layer 110, and exposing part of a surface of the metal layer ML2.

It is particularly noted that, in the embodiment, the microfluidic channel MC1 and the metal layer ML1 may be of the same layer, the microfluidic channel MC2 and the metal layer ML2 may be of the same layer, and the micro via holes 110*h* and the bridge patterns BP1 may be of the same layer. More specifically, the insulation layer 110 defines the microfluidic channel MC1 and the micro via holes 110*h*, and the insulation layer 130 defines the microfluidic channel MC2.

In the stacking direction of the plurality of metal layers, a height H1 of the microfluidic channel MC1 is substantially equal to a thickness t1 of the metal layer ML1, and a height H2 of the microfluidic channel MC2 is substantially equal to a thickness t2 of the metal layer ML2. Preferably, the height H1 of the microfluidic channel MC1 and the height H2 of the microfluidic channel MC2 can each be in the range of 0.05 micrometers to 20 micrometers. In any direction parallel to the substrate surface 50*s* (e.g., direction X), the hole width Wh of the micro via hole 110*h* is substantially equal to the pattern width Wp of the bridge pattern BP1.

It should be noted first that the microfluidic channel MC1, the microfluidic channel MC2 and the micro via holes 110*h* are respectively formed by etching part of the metal layer ML1, part of the metal layer ML2 and part of the bridge patterns BP1. That is, the microfluidic channels and micro via holes of present invention are formed after the formation of the metal layers and the bridge patterns.

In the embodiment, the circuit structure layer 100 further includes a metal layer ML3, an insulation layer 120 and a plurality of bridge patterns BP2*a* and BP2*b*. The metal layer ML3 is disposed between the semiconductor substrate 50 and the metal layer ML1. The insulation layer 120 is disposed between the metal layer ML1 and the metal layer ML3. The bridge patterns BP2*a* and BP2*b* penetrate the insulation layer 120 and are electrically connected to the metal layer ML3. It is particularly noted that the bridge pattern BP2*a* is also electrically connected to the metal layer ML1, that is, the metal layer ML1 and the metal layer ML3 are electrically connected to each other through the bridge pattern BP2*a*. Microfluidic channel MC1 exposes the bridge patterns BP2*b*.

As shown in FIG. 1, in any direction (e.g., direction X) parallel to the substrate surface 50*s*, the width of the bridge pattern BP2*b* is different from the width of the bridge pattern BP2*a*, but the disclosure is not limited thereto. In another modified embodiment, each bridge pattern passing penetrating the same insulation layer may have the same width.

It should be noted that although FIG. 1 only illustrates three metal layers for exemplary explanation, it does not mean that the present invention is limited thereto. In order to meet different three-dimensional circuit design requirements, the circuit structure layer 100 can also be provided with more metal layers, that is, the number of metal layers can be more than three, such as six or nine. For example, a film stack structure 105 composed of at least one metal layer (not shown) and at least one insulation layer (not shown) may be disposed between the metal layer ML3 and the semiconductor substrate 50 in FIG. 1. The film stack structure 105 is also used to form the three-dimensional circuit of the circuit structure layer 100.

Furthermore, in the embodiment, the metal layer ML1, the metal layer ML2, and the metal layer ML3 may have the conductive pattern CP1, the conductive pattern CP2, and the conductive pattern CP3 respectively. The conductive pattern CP1 is electrically connected to the conductive pattern CP3 via the bridge pattern BP2*a*, and is electrically connected to the conductive pattern CP2 via the bridge pattern BP1. In addition, the metal layer ML3 further includes a signal trace SL1 and a signal trace SL2 electrically independent of each other, and the two signal traces are electrically connected to the bridge patterns BP2*b* respectively. The signal trace SL1 and the signal trace SL2 are each electrically connected to at least three bridge patterns BP2*b*, but the disclosure is not limited thereto.

Specifically, the conductive pattern CP2 may be used as a pad of the semiconductor chip embedded with microfluidic channels for inputting or outputting electrical signals, and the number thereof may be multiple. For example, the semiconductor chip 10 with embedded microfluidic channels may be wire bonded to a circuit board (not shown) through a plurality of conductive patterns CP2 to receive control signals from the circuit board or transmit measurement signals to circuit board.

In the embodiment, the semiconductor chip 10 with embedded microfluidic channels is suitable for measuring the resistance or impedance of the fluid in the microfluidic channel MC1. The bridge patterns BP2*b* electrically connected to the signal trace SL1 and the signal trace SL2 may be used as a driving electrode and a sensing electrode during impedance/resistance measurement. For example, the aforementioned driving electrode may be electrically coupled to an output terminal of an impedance analyzer via the signal trace SL1 and one conductive pattern CP2 corresponding thereto, and the aforementioned sensing electrode may be electrically coupled to an input terminal of the impedance analyzer via the signal trace SL2 and another conductive pattern CP2 corresponding thereto.

The following will exemplarily describe a method of fabricating the semiconductor chip with embedded microfluidic channels.

Figure 2A:
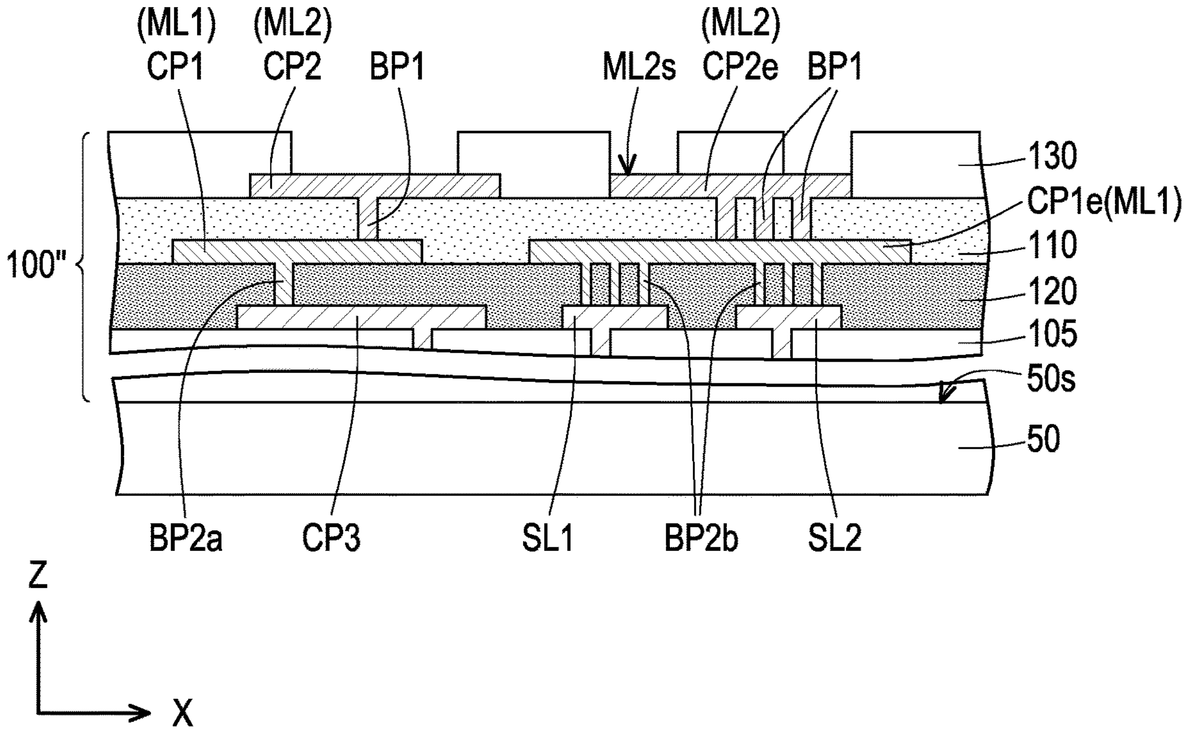
FIG. 2A to FIG. 2E are cross-sectional views of a process of fabricating the semiconductor chip with embedded microfluidic channels of FIG. 1.

Referring to FIG. 2A, first, forming a circuit structure layer 100" on the semiconductor substrate 50. The step of forming the circuit structure layer 100" includes, for example, sequentially forming a metal layer ML3, an insulation layer 120, a metal layer ML1, an insulation layer 110, a metal layer ML2 and an insulation layer 130 on the substrate surface 50*s* of the semiconductor substrate 50. The materials of the metal layer ML1, the metal layer ML2 and the metal layer ML3 include, for example, aluminum, copper, molybdenum or titanium. The materials of the insulation layer 110, the insulation layer 120 and the insulation layer 130 include, for example, silicon dioxide, silicon nitride or silicon oxynitride.

For example, during the formation process of the metal layer ML1, a plurality of bridge patterns BP2*a* and BP2*b* penetrating the insulation layer 120 may be formed simultaneously. During the formation process of the metal layer ML2, a plurality of bridge patterns BP1 penetrating the insulation layer 110 may be formed simultaneously. That is, in the embodiment, the materials of the bridge patterns BP2*a*, BP2*b* and the metal layer ML1 may be selectively the same, and the materials of the bridge patterns BP1 and the metal layer ML2 may be selectively the same. However, the present invention is not limited thereto. In other embodiments, the materials of the bridge pattern and the metal layer may be selectively different. For example, the bridge pattern may be formed by using gold, silver, silver/silver chloride, metal alloys with high silver content, or metal compounds containing tungsten. That is, the bridge pattern and the metal layer may be formed separately.

It is particularly noted that the step of forming the metal layer ML1 may include forming the conductive pattern CP1 and the conductive pattern CP1*e* simultaneously. The step of forming the metal layer ML2 may include forming the conductive pattern CP2 and the conductive pattern CP2*e* simultaneously. The conductive pattern CP2*e* is electrically connected to the conductive pattern CP1*e* via the bridge patterns BP1. The conductive pattern CP1*e* is electrically connected to the signal trace SL1 and the signal trace SL2 of the metal layer ML3 through the bridge patterns BP2*b*.

In the embodiment, the film stack structure 105 may be formed on the semiconductor substrate 50 before forming the metal layer ML3. For clarity, FIG. 2A omits the detailed structure of the film stack structure 105. The omitted part includes, for example, at least one metal layer and at least one insulation layer to form a more complex three-dimensional circuit. However, the disclosure is not limited thereto. In other embodiments, the fabrication of the film stack structure 105 may be omitted for the circuit structure layer.

Figure 2B:
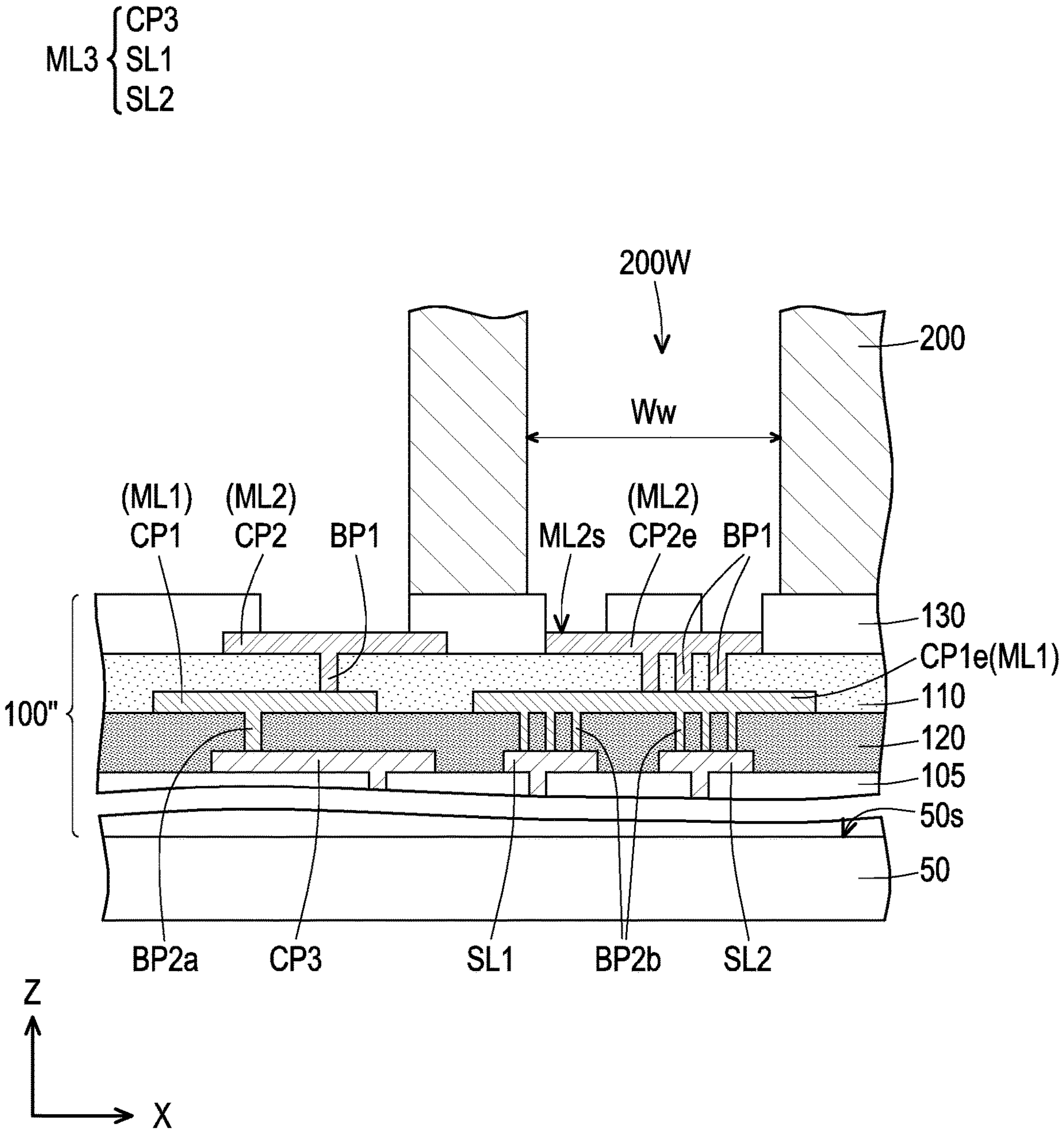

Referring to FIG. 2B, after the production of the circuit structure layer 100" is complete, a wet etching process is performed to remove part of the metal layer ML1, part of the metal layer ML2 and at least one of the bridge patterns BP1. It should be noted that an elastomer layer 200 may be disposed on the circuit structure layer 100" before the wet etching process. The elastomer layer 200 is disposed on the insulation layer 130 and has a well 200 W exposing part of a surface ML2*s* of the metal layer ML2.

More specifically, the well 200 W of the elastomer layer 200 exposes part of the surface ML2*s* of the conductive pattern CP2*e* of the metal layer ML2. That is, in the stacking direction of the plurality of metal layers, the well 200 W does not overlap the conductive pattern CP2 of the metal layer ML2. In the embodiment, the material of the elastomer layer 200 includes, for example, polydimethylsiloxane (PDMS) or other materials with an elastic modulus less than or equal to 5 MPa. However, the present invention is not limited thereto. In other embodiments, the elastomeric layer 200 may be replaced by a non-elastomeric layer.

Figure 2C:
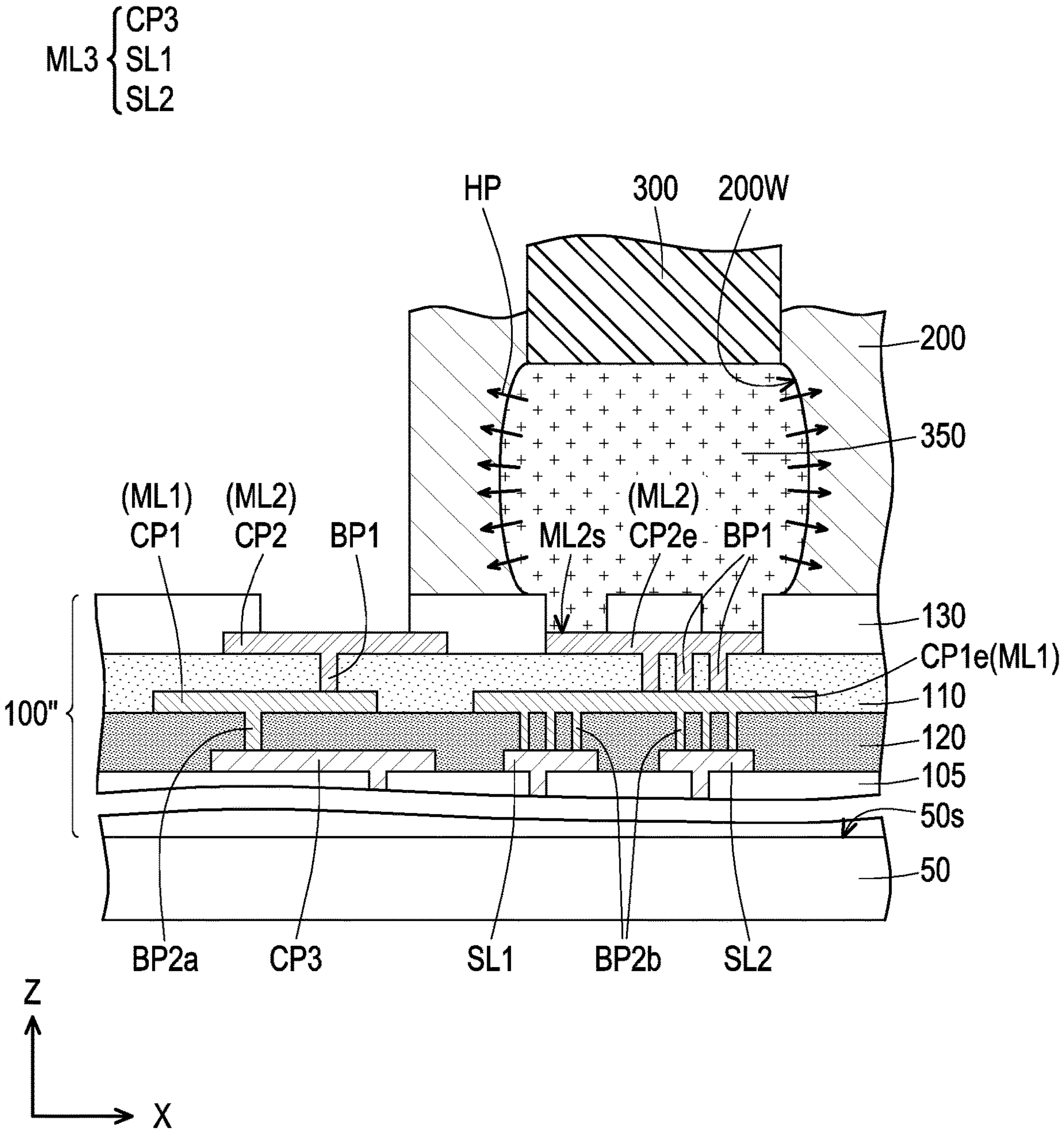

Referring to FIGS. 2B and 2C, the steps of the wet etching process may include injecting an etchant 350 through the well 200 W of the elastomer layer 200, and the etchant 350 is suitable for removing part of the metal layer ML1, part of the metal layer ML2 and at least one of the bridge patterns BP1. The material of the etchant 350 includes, for example, phosphoric acid and hydrogen peroxide, or other etchants suitable for etching metal.

For example, in the embodiment, a width Ww of the well 200 W along any direction parallel to the substrate surface 50*s* is, for example, 1 mm, and the well 200 W is suitable for inserting the syringe 300. In particular, since the size of the conductive pattern CP2*e* is similar to the size of the other conductive pattern CP2 serving as a pad, the alignment accuracy requirement of the well 200 W of the elastomer layer 200 on the circuit structure layer 100" does not need to be too high. As long as the conductive pattern CP2*e* of the metal layer ML2 is adequately covered by the well 200 W of the elastomer layer 200, successful delivery of the etchant 350 is assured.

In order to improve the etching efficiency of the etchant 350, the steps of the wet etching process may also include increasing the hydraulic pressure HP of the etchant 350 in the well 200 W. Since the elastomer layer 200 is elastic, the pressure used to increase the hydraulic pressure HP causes the elastomer layer 200 to deform, thereby effectively converting the pressure into elastic potential energy and storing it in the elastomer layer 200. From another perspective, the deformed elastomer layer 200 may continuously exert such pressure to ensure that the enhanced etching rate can be maintained throughout the etching process.

Figure 2D:
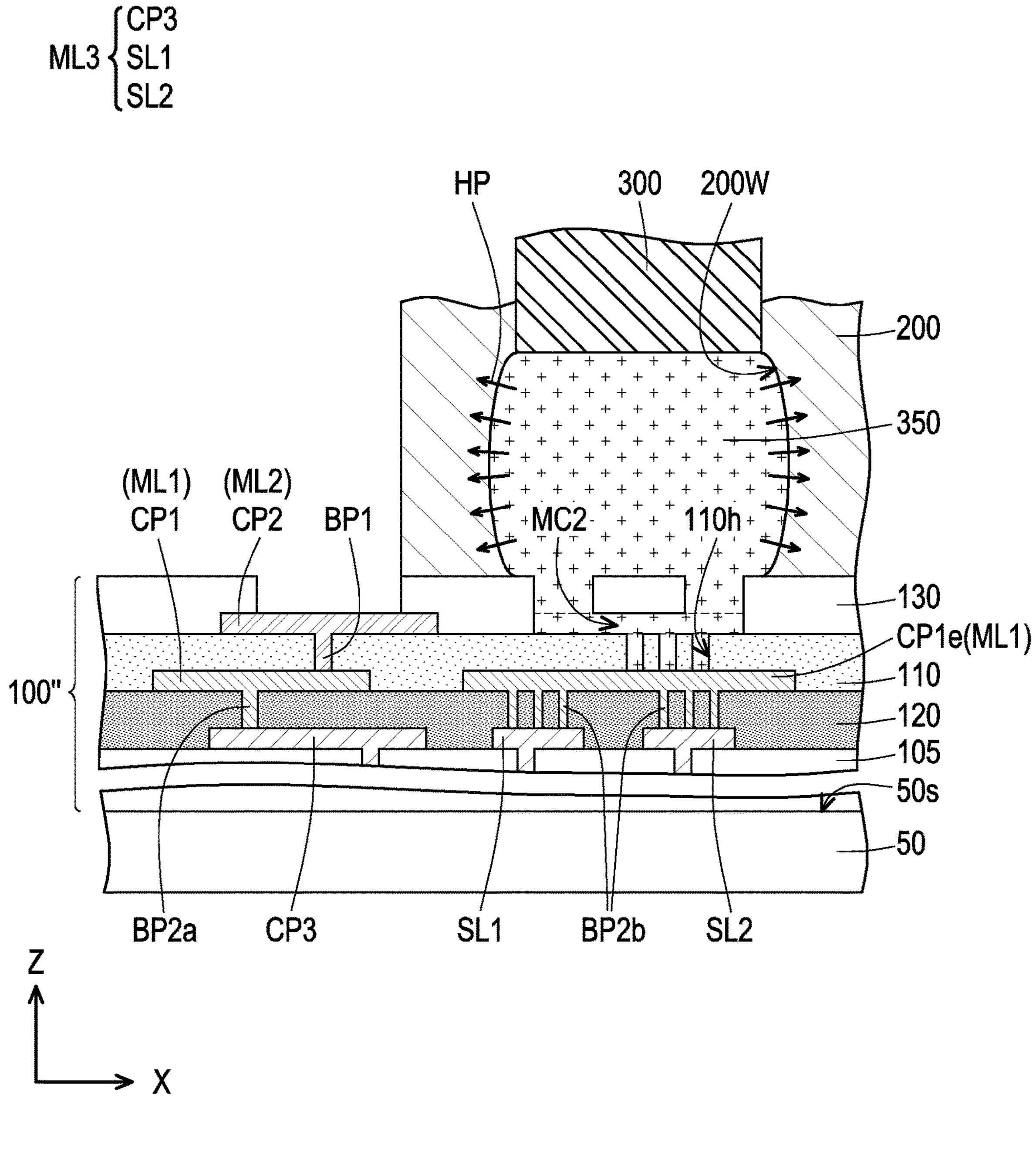
Figure 2E:
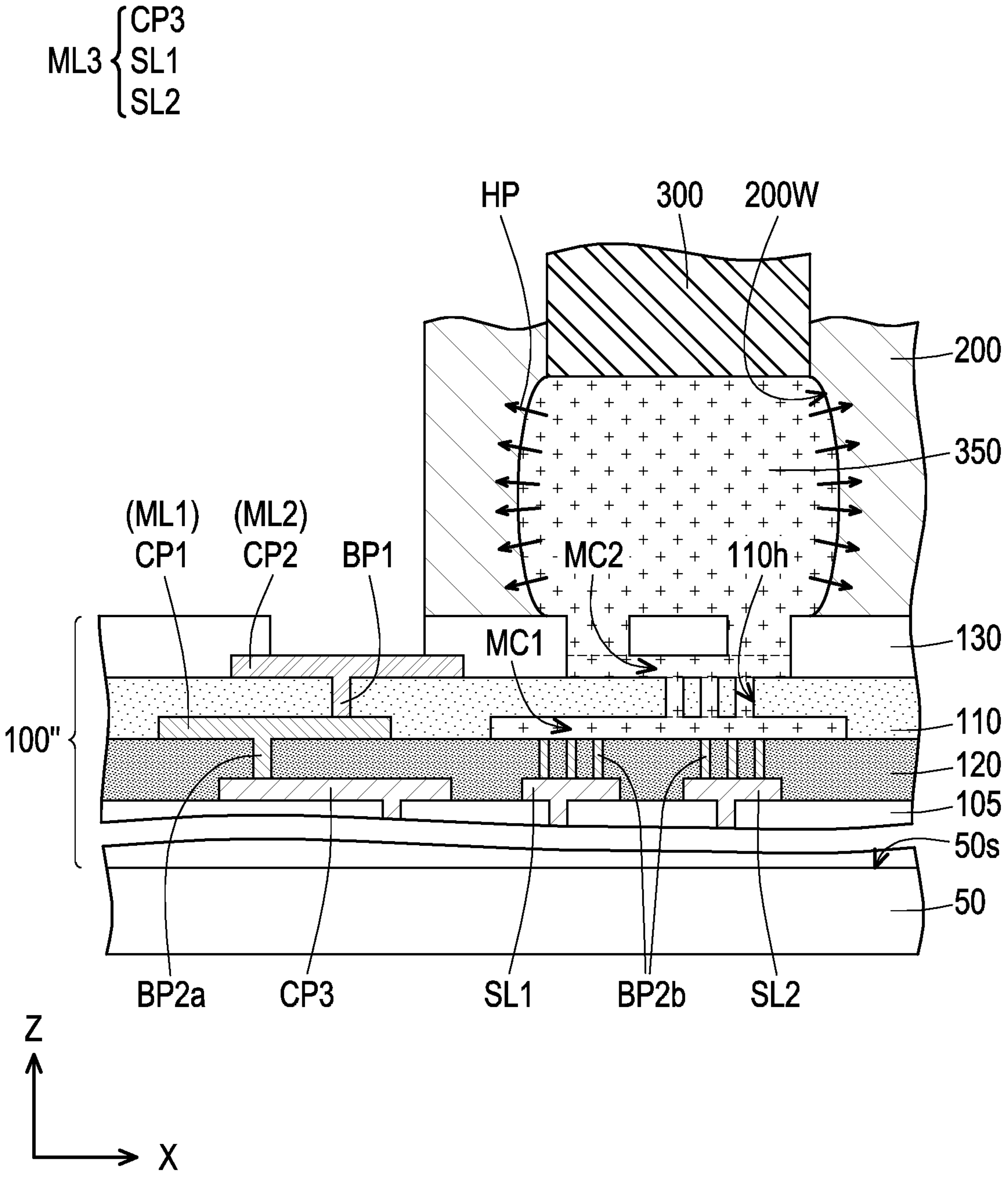

During the wet etching process of the embodiment, the conductive pattern CP2*e* of the metal layer ML2, at least one of the bridge patterns BP1 and the conductive pattern CP1*e* of the metal layer ML1 are sequentially removed by the etchant 350 to form a microfluidic channel MC2, at least one of micro via hole 110*h* and microfluidic channel MC1, respectively, as shown in FIG. 2D and FIG. 2E.

In order to prevent the etchant 350 from over-etching the bridge patterns BP2*b*, the impedance between the bridge patterns BP2*b* may be measured in real-time during the entire wet etching process. For example, a part of the bridge patterns BP2*b* electrically connected to the signal trace SL1 may serve as a driving electrode during impedance measurement, and another part of the bridge patterns BP2*b* electrically connected to the signal trace SL2 may serve as a sensing electrode during impedance measurement.

Referring to FIGS. 3A to 3C, during the process of the etchant 350 etching the conductive pattern CP1*e* of the metal layer ML1, the impedance between the driving electrode and the sensing electrode changes with the thickness of the conductive pattern CP1*e*. For example, the conductive pattern CP1*e* in phase I (as shown in FIG. 3A), phase II (as shown in FIG. 3B) and phase III (as shown in FIG. 3C) of the etching process respectively have thickness ta, thickness tb and thickness tc that decrease in sequence.

Referring to FIG. 4, in phase I, since the thickness ta of the conductive pattern CP1*e* is similar to initial thickness thereof (for example, the thickness t1 of the conductive pattern CP1 in FIG. 1), both electrodes (i.e. driving electrode and sensing electrode) are shorted by the conductive pattern CP1*e*. The impedance Za measured in phase I is essentially dominated by the measurement circuit. In phase II, since the thickness tb of the conductive pattern CP1*e* is significantly different from initial thickness thereof, the impedance Zb measured in phase II increases significantly compared with the impedance Za in phase I. The significant change of impedance from phase I to phase II is mainly caused by the change of the dominant impedance, for example, the main contribution of the impedance changes from the measurement circuit to the significantly thinner conductive pattern CP1*e*. In phase III, when the conductive pattern CP1*e* is further etched to make the thickness tc thereof almost nonexistent, the measured impedance dramatically increase from the impedance Zb in phase II to the impedance Zc.

Once the impedance between the driving electrode and the sensing electrode is greater than or equal to a predetermined value, the wet etching process is halted. In the embodiment, the predetermined value may be equal to or slightly greater than the impedance Zc, but the disclosure is not limited thereto. Accordingly, over-etching of the bridge patterns BP2*b* connected to the conductive pattern CP1*e* may be avoided. Herein, the fabrication of the semiconductor chip 10 embedded with microfluidic channels of the embodiment is complete.

In the embodiment, the microfluidic channels and the micro via holes of the semiconductor wafer 10 embedded with microfluidic channels are formed by wet etching part of the metal layers and the bridge patterns pre-formed in the circuit structure layer. Therefore, the microfluidic structure (i.e., the combination of microfluidic channels and micro via holes) has excellent integration with the semiconductor chip, and the manufacturing cost is reduced. From another point of view, since the microfluidic structure of the embodiment is defined by the metal layers and the bridge patterns in the circuit structure layer of the semiconductor chip, the fineness and complexity of its structure may depend on the current semiconductor process capabilities.

Some other embodiments are provided below to describe the invention in detail, where the same components are denoted by the same referential numbers, and descriptions of the same technical contents are omitted. The aforementioned embodiment may be referred for descriptions of the omitted parts, and detailed descriptions thereof are not repeated in the following embodiments.

Figure 5A:
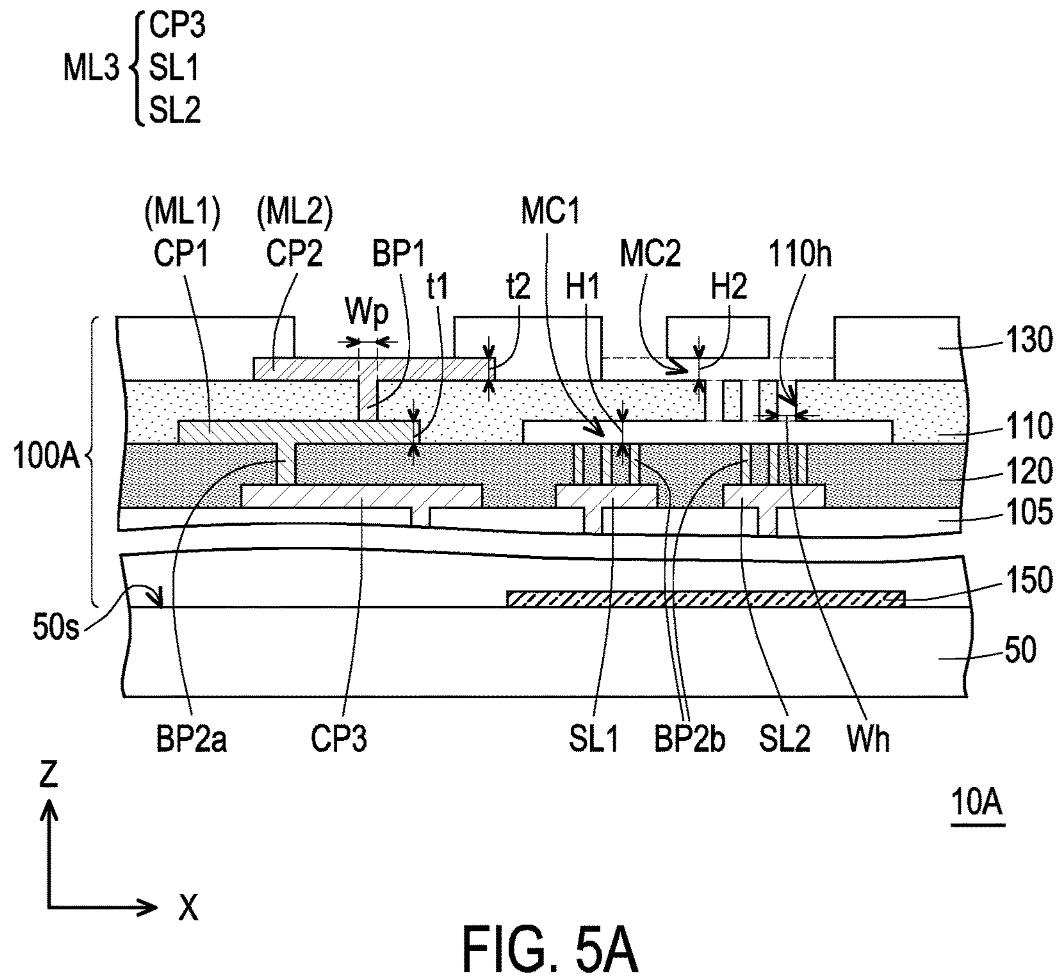
FIG. 5A is a schematic cross-sectional view of a semiconductor chip with embedded microfluidic channels according to a second embodiment of the disclosure.

FIG. 5A is a schematic cross-sectional view of a semiconductor chip with embedded microfluidic channels according to a second embodiment of the disclosure. FIG.

Figure 6:
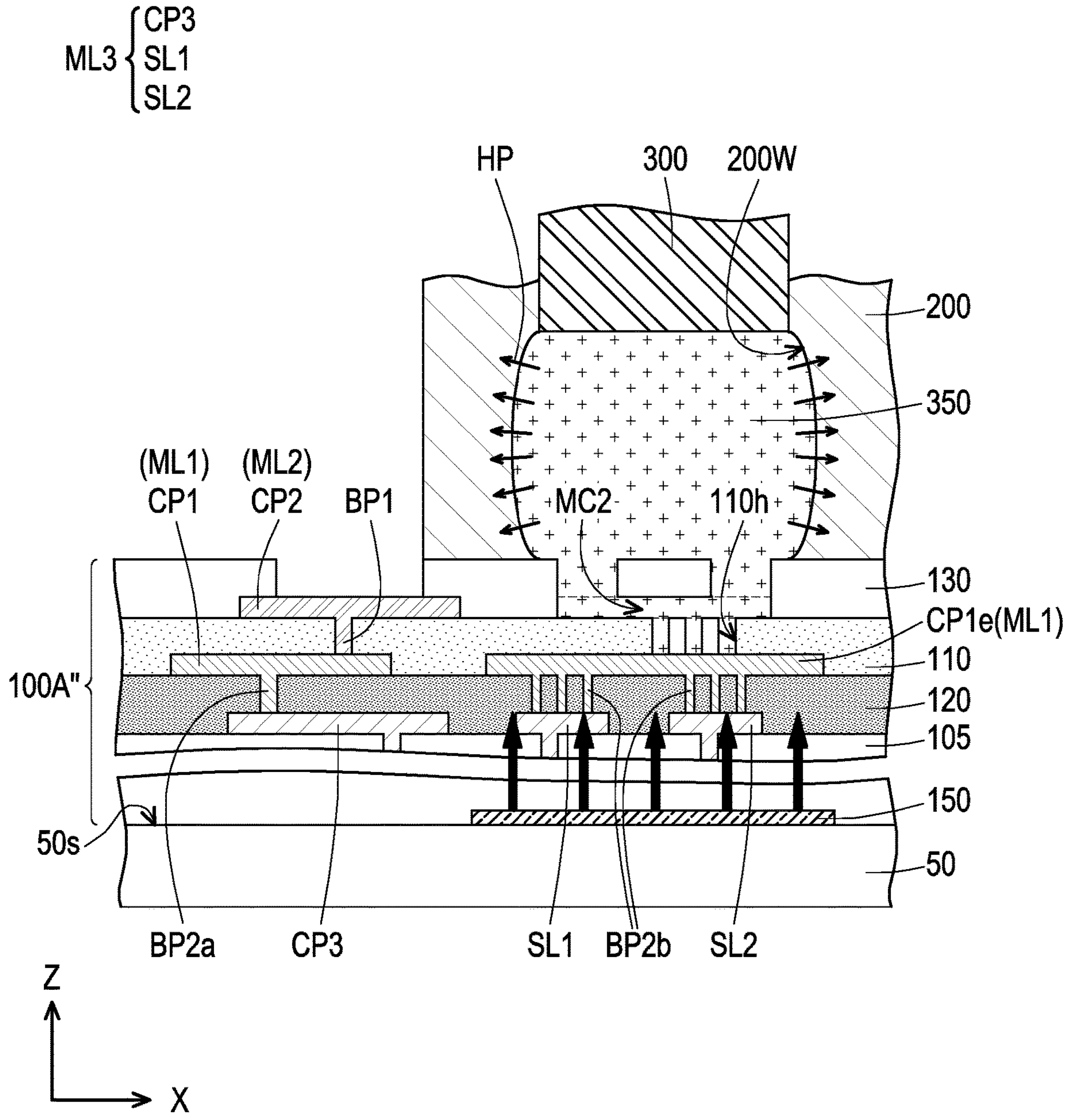
FIG. 6 is a schematic cross-sectional view of the semiconductor chip with embedded microfluidic channels in FIG. 5A during a wet etching process.

5B is a schematic diagram of another modified embodiment of the semiconductor chip with embedded microfluidic channels of FIG. 5A. FIG. 6 is a schematic cross-sectional view of the semiconductor chip with embedded microfluidic channels in FIG. 5A during a wet etching process. Referring to FIG. 5A, the difference between the semiconductor chip 10A with embedded microfluidic channels of present embodiment and the semiconductor chip 10 with embedded microfluidic channels in FIG. 1 is that the semiconductor chip 10A with embedded microfluidic channels may optionally further include a heater 150 embedded in the circuit structure layer 100A.

In the embodiment, the heater 150 may be disposed on the substrate surface 50*s* of the semiconductor substrate 50. More specifically, the heater 150 may be composed of a metal layer of the film stack structure 105, but the disclosure is not limited thereto. The heater 150 may also be made of polysilicon material, metal or alloy.

Figure 5B:
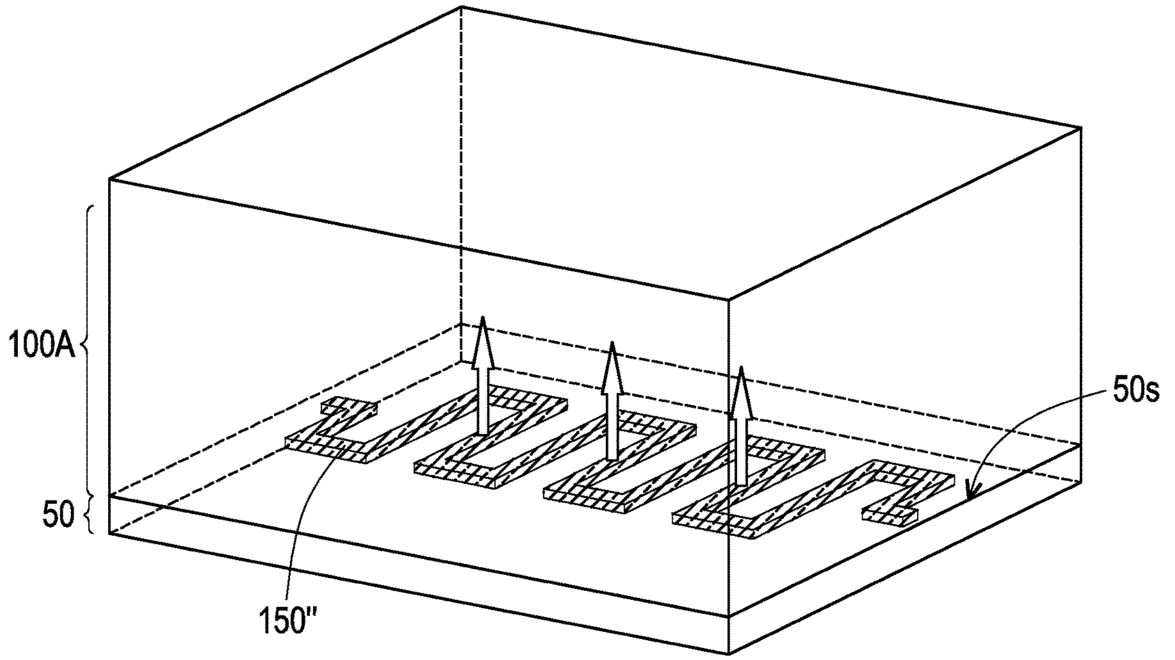
FIG. 5B is a schematic diagram of another modified embodiment of the semiconductor chip with embedded microfluidic channels of FIG. 5A.

On the other hand, the heater 150 may overlap the microfluidic channel MC1, the microfluidic channel MC2 and the micro via holes 110*h* (or the flow path of the etchant) along the stacking direction of the metal layers (i.e., the direction Z), but the disclosure is not limited thereto. In other embodiments, the heater does not have to overlap the microfluidic structure, as long as it is close to the microfluidic structure. Alternatively, the heater may be placed at a position where the entire circuit structure layer can be heated. As shown in FIG. 5B, in another modified embodiment, the heater 150" disposed on the substrate surface 50*s* may have a meander structure to increase the resistance and heat the entire circuit structure layer 100A.

Specifically, during the process of removing part of the metal layers and the bridge patterns with the etchant 350, the heater 150 embedded in the circuit structure layer 100A" is used to heat the etchant 350 (as shown in FIG. 6), so as to effectively improve the etching efficiency of the wet etching process. In order to stably control the temperature of the etchant 350 during the etching process, the circuit structure layer 100A can also be provided with a feedback circuit (not shown) to dynamically adjust the heating power of the heater 150 according to the temperature measured in real-time.

Figure 7:
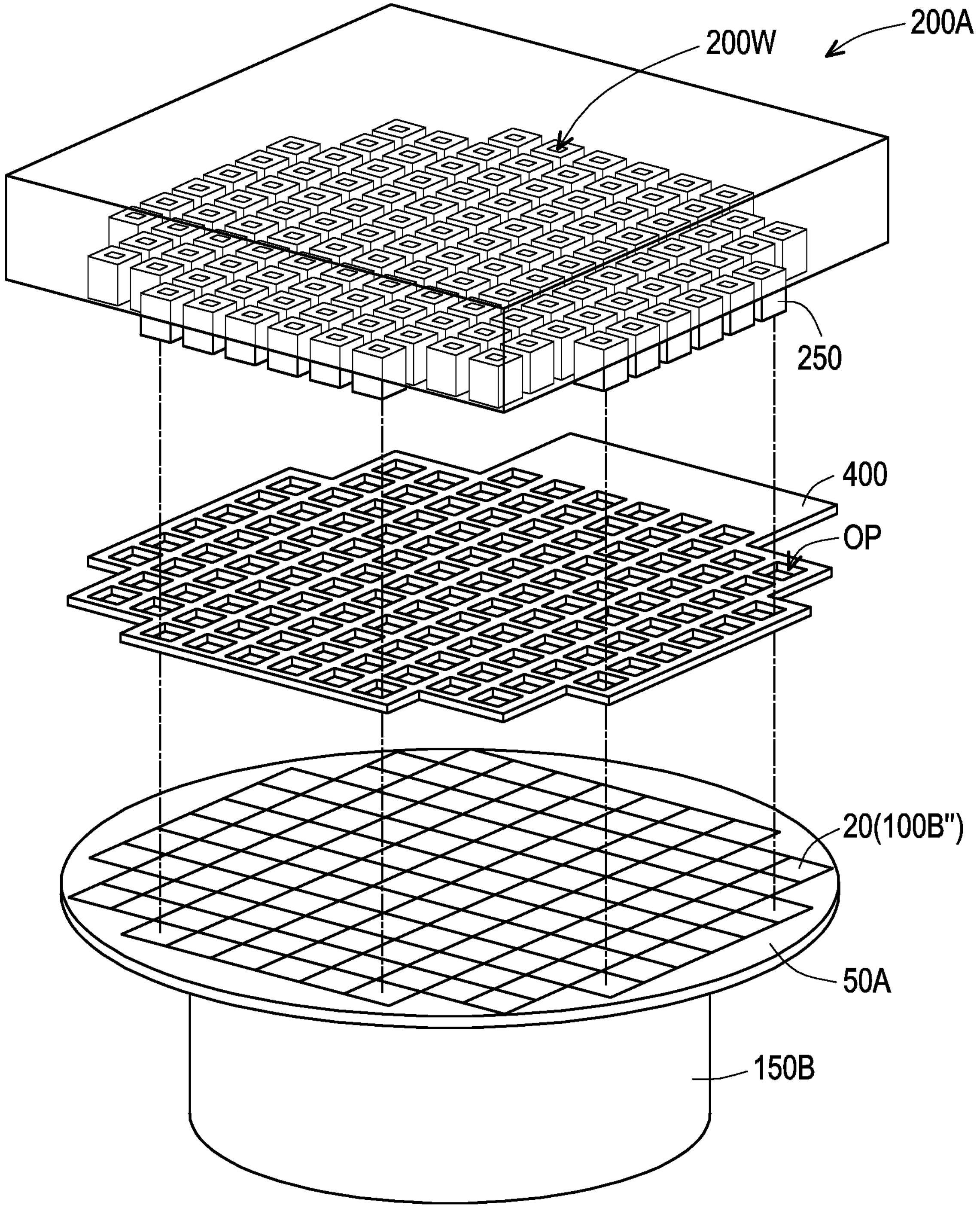
FIG. 7 is a schematic diagram of a manufacturing equipment for a plurality of semiconductor chips with embedded microfluidic channels according to a third embodiment of the disclosure.
Figure 8:
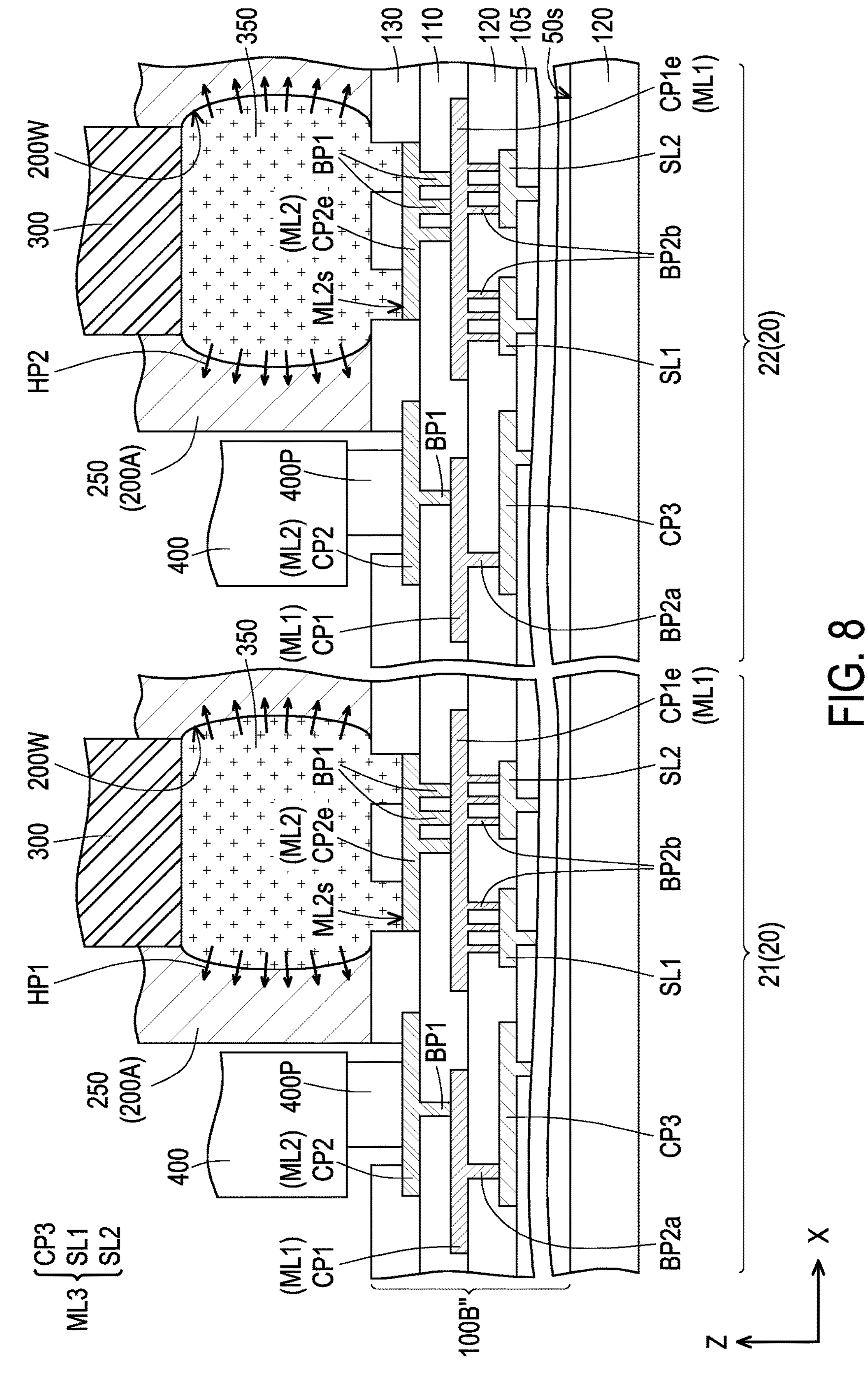
FIG. 8 is a schematic cross-sectional view of two die units in FIG. 7 during a wet etching process.

FIG. 7 is a schematic diagram of a manufacturing equipment for a plurality of semiconductor chips with embedded microfluidic channels according to a third embodiment of the disclosure. FIG. 8 is a schematic cross-sectional view of two die units in FIG. 7 during a wet etching process. It is particularly noted that although FIGS. 2B to 2E only illustrate a wet etching process for a single semiconductor chip, they are also applicable to a wafer-level process.

Referring to FIG. 7 and FIG. 8, in the embodiment, the semiconductor substrate 50A is, for example, a silicon wafer, and the circuit structure layer 100B" thereon may include a plurality of die units 20. In order to perform the aforementioned wet etching process for the die units 20 simultaneously, the elastomer layer 200A provided on the circuit structure layer 100B" may have a plurality of posts 250. The plurality of posts 250 are respectively arranged corresponding to the plurality of die units 20. More specifically, each post 250 is provided with a well 200 W, and the well 200 W of each post 250 is arranged to overlap a corresponding die unit 20. During a wet etching process, the well 200 W of each post 250 is suitable for injecting an etchant for removing part of the metal layer.

On the other hand, in the embodiment, the manufacturing equipment used in the wet etching process may further include a detector 400 and a heater 150B. For example, the detector 400 may be disposed between the elastomer layer 200A and the semiconductor substrate 50A, and has a plurality of openings OP adapted to allow the plurality of posts 250 of the elastomer layer 200A to pass through and a plurality of probe pins 400P configured to electrically contact a plurality of pads (e.g., the conductive pattern CP2) of the die unit 20.

The detector 400 is adapted to monitor the impedance between the driving electrode (e.g., a plurality of bridge patterns BP2*b* connected to the signal trace SL1) and the sensing electrode (e.g., a plurality of bridge patterns BP2*b* connected to the signal trace SL2) in real-time during the wet etching process of the die units 20 to determine the etching progress of each die unit 20. Since the method of monitoring the etching progress by measuring the impedance in the embodiment is similar to the embodiment of FIGS. 3A to 3C and FIG. 4, please refer to the relevant paragraphs of the foregoing embodiments for detailed description, which will not be described again herein.

Furthermore, during the wet etching process of the embodiment, the hydraulic pressure of the etchant 350 in the well 200 W of each of the posts 250 may be increased individually. Referring to FIG. 8, for example, when the etching progress of the die unit 22 lags behind the etching progress of the die unit 21, the hydraulic pressure HP2 of the etchant 350 in the well 200 W of the post 250 provided corresponding to the die unit 22 can be increased or reduce the hydraulic pressure HP1 of the etchant 350 in the well 200 W of the post 250 provided corresponding to the die unit 21 to reduce the difference in etching progress between the two die units 21, 22.

On the other hand, a heater 150B disposed under the semiconductor substrate 50A (as shown in FIG. 7) can heat the etchant 350 to improve the etching efficiency of the wet etching process.

Figure 9:
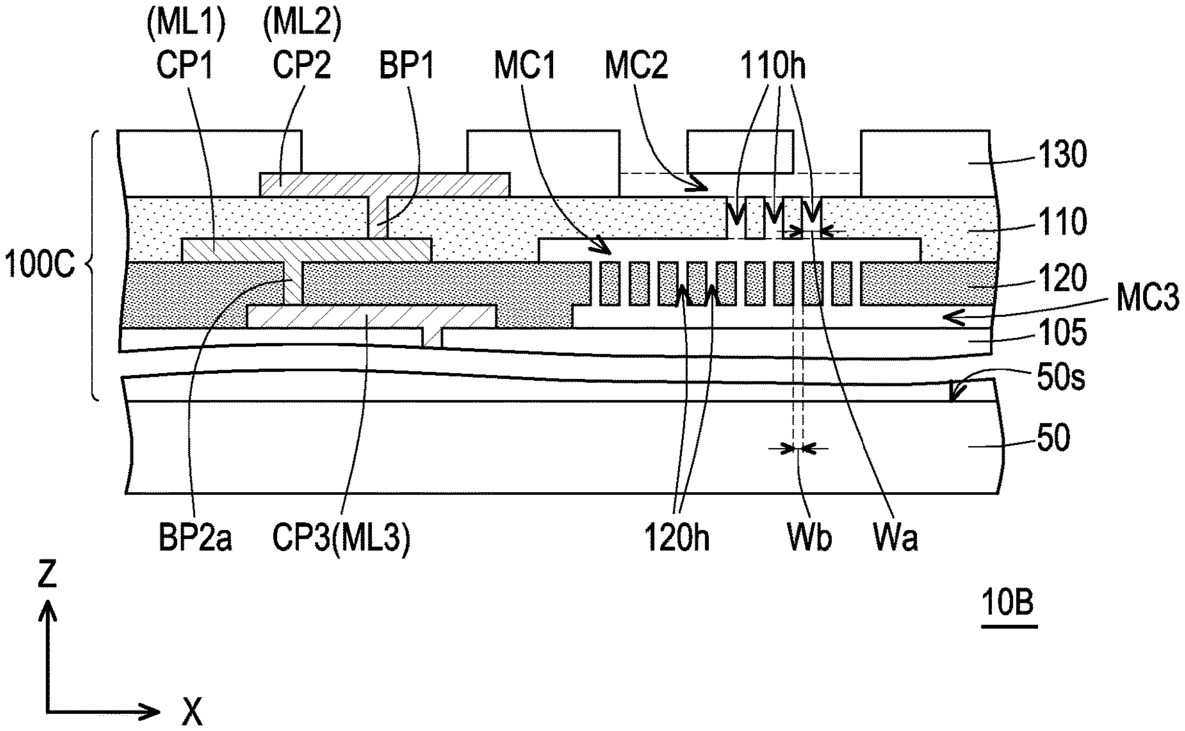
FIG. 9 is a schematic cross-sectional view of a semiconductor chip with embedded microfluidic channels according to a fourth embodiment of the disclosure.

FIG. 9 is a schematic cross-sectional view of a semiconductor chip with embedded microfluidic channels according to a fourth embodiment of the disclosure. Referring to FIG. 9, compared with the semiconductor chip 10 with embedded microchannels in FIG. 1, the circuit structure layer 100C of the semiconductor chip 10B with embedded microchannels of the embodiment further includes a microfluidic channel MC3 and a plurality of micro via holes 120*h*. The microfluidic channel MC3 is connected to the microfluidic channel MC1 through the micro via holes 120*h*. In the embodiment, the microfluidic channel MC3 and the metal layer ML3 may be of the same layer, and the plurality of micro via holes 120*h* and the bridge pattern BP2*a* may be of the same layer. In other words, the microfluidic channel MC3 is formed by wet etching of part of the metal layer ML3, and the micro via holes 120*h* are formed by wet etching of a plurality of bridge patterns.

It is particularly noted that in any direction parallel to the substrate surface 50*s* (e.g., direction X), a hole width Wb of the micro via hole 120*h* may be less than a hole width Wa of the micro via hole 110*h*. For example, in the embodiment, the plurality of micro via holes 120*h* connected to the microfluidic channel MC1 may be used to filter the whole blood sample, but the disclosure is not limited thereto. Since cells (such as white blood cells, red blood cells, and platelets) can interfere with molecular testing, a centrifuge is generally used to perform chromatography and then the plasma is separated for testing. In the embodiment, filtration of whole blood sample can be performed through the plurality of micro via holes 120*h* embedded in the circuit structure layer 100C. That is, if the size of the cells is greater than the hole width Wb of the micro via holes 120*h*, the cells will stay in the microfluidic channel MC1, and only the plasma can enter the microfluidic channel MC3 through the micro via holes 120*h*.

Figure 10:
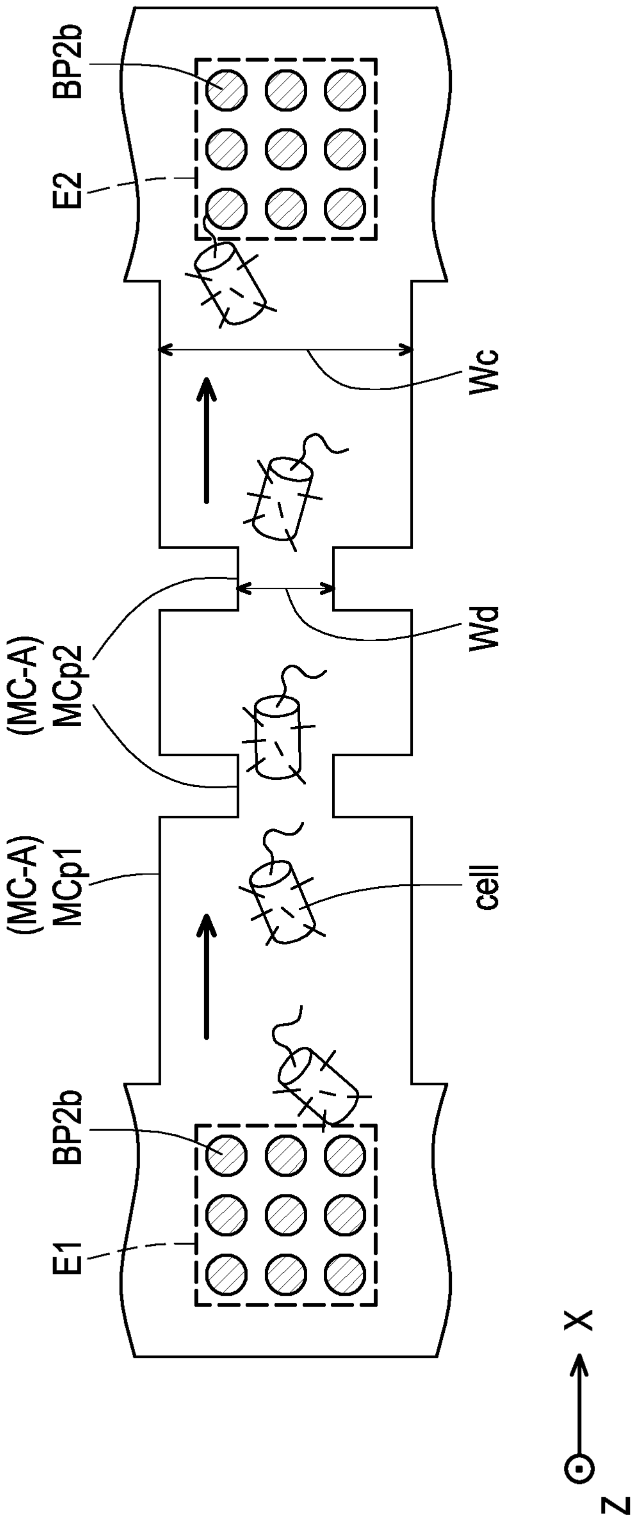
FIG. 10 is a schematic top-view of a microfluidic channel according to one embodiment of the disclosure.

FIG. 10 is a schematic top-view of a microfluidic channel according to one embodiment of the disclosure. Specifically, FIG. 10 illustrates a microfluidic channel design of another modified embodiment of the semiconductor chip 10 with embedded microfluidic channels in FIG. 1. Referring to FIGS. 1 and 10, in the modified embodiment, the microfluidic channel MC-A may include a plurality of first portions MCp1 and a plurality of second portions MCp2 alternately arranged and connected to each other in its extending direction (e.g., direction X).

In a direction perpendicular to the direction X and the direction Z, the first portion MCp1 and the second portion MCp2 of the microfluidic channel MC-A respectively have a width Wc and a width Wd. The width Wc of the first portion MCp1 is greater than the width Wd of the second portion MCp2. In other words, the second portions MCp2 may define the constriction zones of the microfluidic channel MC-A. In the embodiment, the number of constriction zones of the microfluidic channel MC-A is exemplified by taking two as an example, but the disclosure is not limited thereto.

Furthermore, an electrode E1 and an electrode E2 may be respectively provided at both ends of the microfluidic channel MC-A, and these two electrodes may be composed of a plurality of bridge patterns BP2*b* as shown in FIG. 1. The microfluidic channel MC-A with constriction zones is suitable for performing resistive pulse sensing (RPS) of cells. For example, a microfluid containing a plurality of cells may enter the microfluidic channel MC-A from one end provided with the electrode E1 and exit the microfluidic channel MC-A from the other end provided with the electrode E2.

During the process of the cells passing through the microfluidic channel MC-A, the DC ionic resistance across the microfluidic channel MC-A may be measured in real time through the electrodes E1 and E2. When the cells flow through the constriction zones (i.e., the second portion MCp2) of the microfluidic channel MC-A, the measured resistance is increased due to the blocked ion flow and be recorded as a voltage pulse whose pulse width depends on the flow speed of the cells. Through the aforementioned resistive pulse sensing, the size of the cells in the microfluid may be measured.

Figure 11:
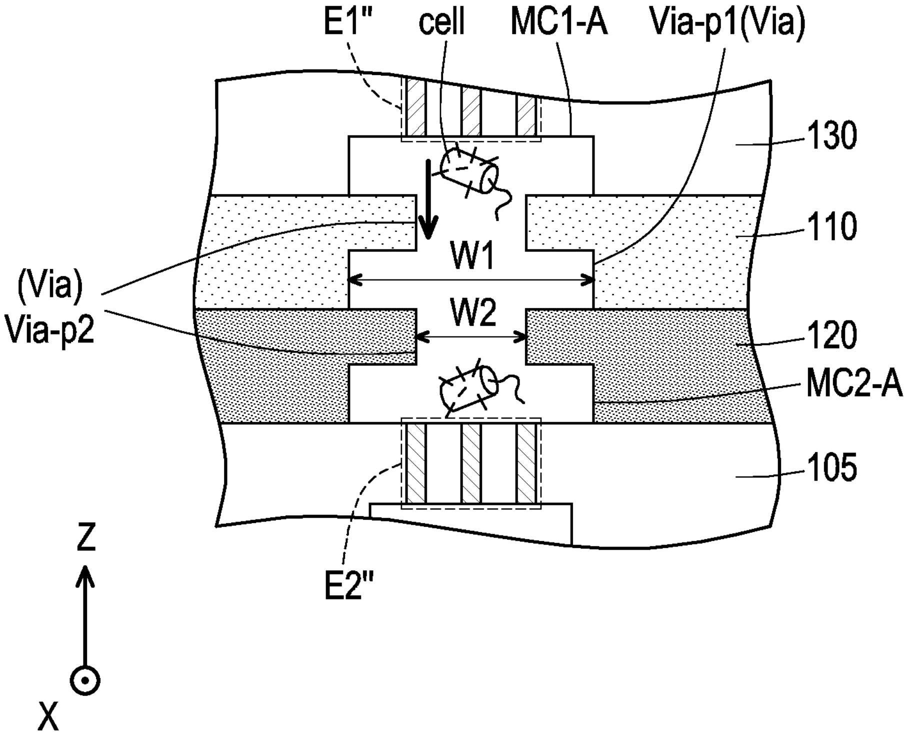
FIG. 11 is a schematic cross-sectional view of a micro via hole according to one embodiment of the disclosure.

FIG. 11 is a schematic cross-sectional view of a micro via hole according to one embodiment of the disclosure. Referring to FIG. 11, in the embodiment, the micro via hole Via may have constriction zones like the microfluidic channel MC-A of FIG. 10. For example, the micro via hole Via connected between the microfluidic channel MC1-A and the microfluidic channel MC2-A may include a first portion Via-p1 and two second portions Via-p2 alternately arranged and connected with each other in its extension direction (e.g., direction Z).

In a direction perpendicular to the direction X and the direction Z, the first portion Via-p1 and the second portion Via-p2 of the micro via hole Via respectively have a width W1 and a width W2. The width W1 of the first portion Via-p1 is greater than the width W2 of the second portion Via-p2. In other words, the second portions Via-p2 may define the constriction zones of the micro via hole Via. In the embodiment, the number of constriction zones of the micro via hole Via is exemplified by taking two as an example, but the disclosure is not limited thereto.

Furthermore, an electrode E1" and an electrode E2" may be respectively provided at both ends of the micro via hole Via. These two electrodes may be composed of a plurality of bridge patterns in different layers of the circuit structure layer, but the present invention is not limited thereto. Similar to the microfluidic channel MC-A in FIG. 10, the micro via hole Via with constriction zones is suitable for performing resistive pulse sensing of cells. For detailed description, please refer to the relevant paragraphs of the foregoing embodiments and will not be described again herein.

Figure 12:
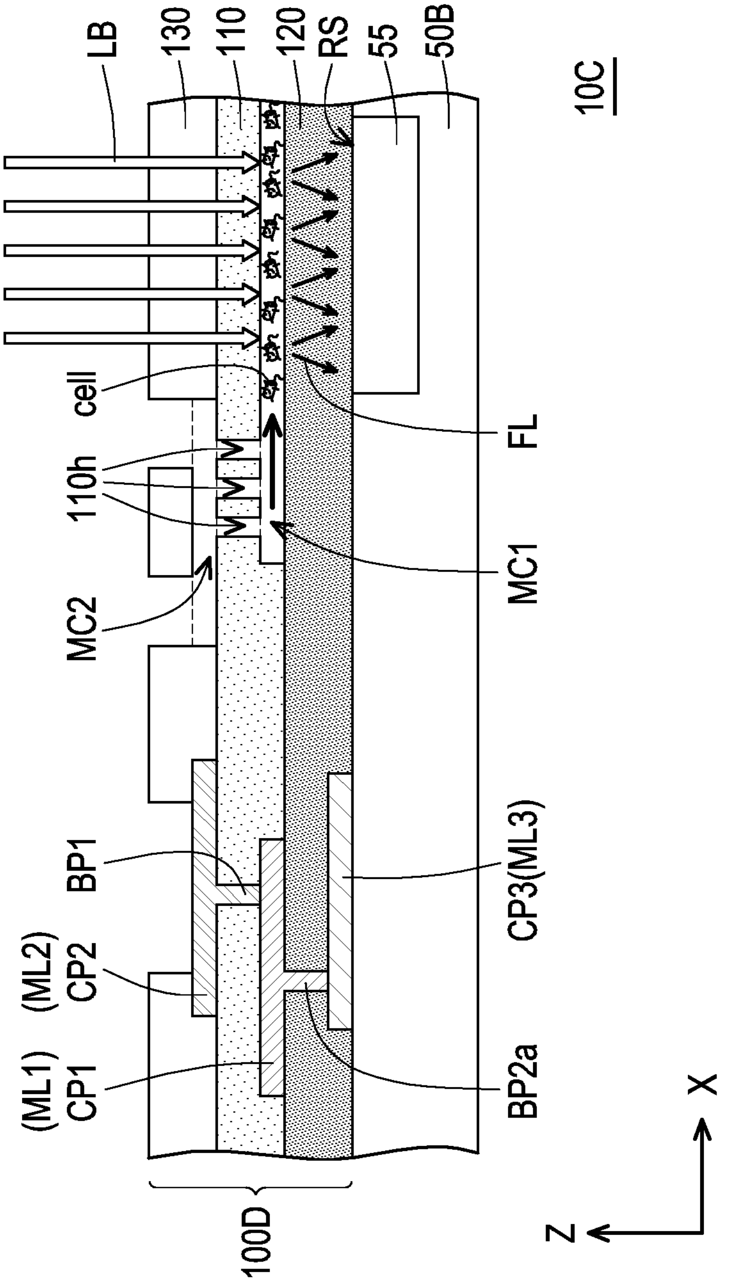
FIG. 12 is a schematic cross-sectional view of a semiconductor chip with embedded microfluidic channels according to a fifth embodiment of the disclosure.

FIG. 12 is a schematic cross-sectional view of a semiconductor chip with embedded microfluidic channels according to a fifth embodiment of the disclosure. Referring to FIG. 12, the main difference between the semiconductor chip 10C with embedded microfluidic channels in the embodiment and the semiconductor chip 10 with embedded microfluidic channels in FIG. 1 lies in the different functionality of the semiconductor chips.

In the embodiment, the semiconductor chip 10C with embedded microfluidic channels may further include an optical sensor 55. The optical sensor 55 is formed on the semiconductor substrate 50B and overlaps the microfluidic channel MC1 of the circuit structure layer 100D along the direction Z. The optical sensor 55 has a receiving surface RS facing the microfluidic channel MC1 and is adapted to receive light from the microfluidic channel MC1. The optical sensor 55 is, for example, a CMOS single-photon avalanche diode (SPAD), but the disclosure is not limited thereto.

The semiconductor chip 10C embedded with microfluidic channels in the embodiment is suitable for detecting the fluorescence reaction of microfluidic samples. For example, a pulsed light source (e.g., a pulsed laser beam LB) may be used to illuminate a microfluid flowing through the microfluidic channel MC1, so that the cells in the microfluid are excited to emit fluorescence FL. The semiconductor chip 10C embedded with the microfluidic channel can detect the fluorescent FL from the cells through the optical sensor 55 and generate the required biological information. Due to the microfluidic channel MC1 of the present disclosure has excellent integration with the semiconductor chip, the microfluidic channel MC1 may be disposed close to the optical sensor 55. Accordingly, the sensing efficiency of the optical sensor 55 may be greatly improved.

Figure 13:
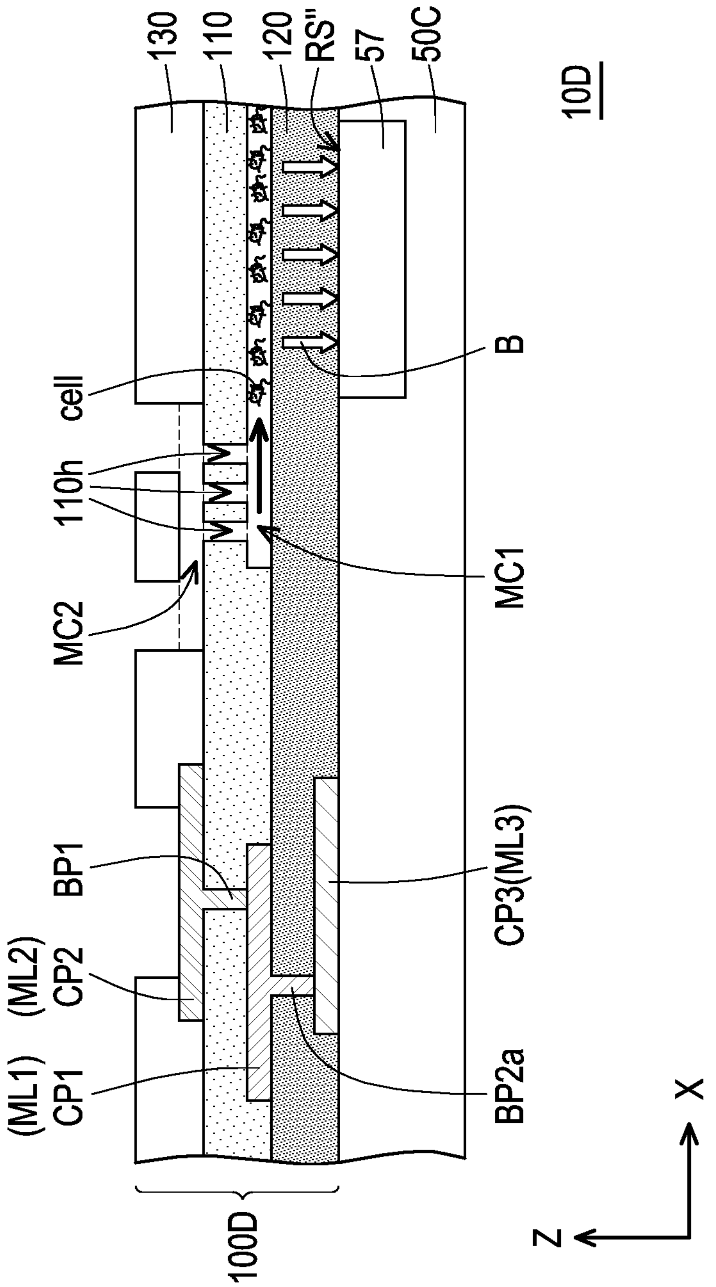
FIG. 13 is a schematic cross-sectional view of a semiconductor chip with embedded microfluidic channels according to a sixth embodiment of the disclosure.

FIG. 13 is a schematic cross-sectional view of a semiconductor chip with embedded microfluidic channels according to a sixth embodiment of the disclosure. Referring to FIG. 13, the main difference between the semiconductor chip 10D embedded with microfluidic channels in the embodiment and the semiconductor chip 10 embedded with microfluidic channels in FIG. 1 lies in the different functionality of the semiconductor chips.

In the embodiment, the semiconductor chip 10D embedded with microfluidic channels may further include a magnetic sensor 57. The magnetic sensor 57 is formed on the semiconductor substrate 50C and overlaps the microfluidic channel MC1 of the circuit structure layer 100D along the direction Z. The magnetic sensor 57 has a receiving surface RS" facing the microfluidic channel MC1, and is adapted to receive the magnetic field B from the microfluidic channel MC1. The magnetic sensor 57 is, for example, a CMOS magnetic hall sensor, but the disclosure is not limited thereto.

The semiconductor chip 10D embedded with microfluidic channels of the embodiment is suitable for molecular recognition of microfluidic samples. For example, as cells bound with magnetic beads and flowing in the microfluidic channel MC1 pass over the magnetic sensor 57, the magnetic field generated by the magnetic beads act on the magnetic sensor 57, which changes the output voltage signal to achieve the purpose of molecular recognition. Due to the microfluidic channel MC1 of the present disclosure has excellent integration with the semiconductor chip, the microfluidic channel MC1 may be disposed close to the magnetic sensor 57. Accordingly, the sensing efficiency of the magnetic sensor 57 can be greatly improved.

In summary, in the semiconductor chip with embedded microfluidic channels and the method of fabricating the same according to an embodiment of the disclosure, a wet etching process can be used to remove part of the metal layers and the bridge patterns formed in the circuit structure layer on the semiconductor substrate to form connected microfluidic channels and micro via holes. Therefore, the microfluidic structure of present disclosure has excellent integration with the semiconductor chip, and the manufacturing cost may be reduced. In addition, the fineness and complexity of microfluidic structures may also be improved by the capabilities of current semiconductor manufacturing process.

It will be apparent to those skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:

1. A semiconductor chip with embedded microfluidic channels, comprising:
- a semiconductor substrate;
- a circuit structure layer, comprising:
  - a first metal layer, disposed on a substrate surface of the semiconductor substrate;
  - a second metal layer, disposed on the first metal layer along a stacking direction;
  - a first insulation layer, disposed between the first metal layer and the second metal layer; and
  - a plurality of first bridge patterns, penetrating the first insulation layer, and each electrically connected to at least one of the first metal layer and the second metal layer;
- a first microfluidic channel, embedded in the circuit structure layer, and located between the second metal layer and the semiconductor substrate; and
- a micro via hole, embedded in the circuit structure layer, and connected to the first microfluidic channel, wherein an extending direction of the micro via hole intersects the substrate surface of the semiconductor substrate and an extending direction of the first microfluidic channel, a first height of the first microfluidic channel along the stacking direction is equal to a first thickness of the first metal layer along the stacking direction, a hole width of the micro via hole along any direction parallel to the substrate surface is equal to a pattern width of each of the first bridge patterns along the any direction parallel to the substrate surface.

2. The semiconductor chip with embedded microfluidic channels according to claim 1, wherein the circuit structure layer further comprises:
- a third metal layer, disposed between the semiconductor substrate and the first metal layer;
- a second insulation layer, disposed between the first metal layer and the third metal layer; and
- a plurality of second bridge patterns, penetrating the second insulation layer, and each electrically connected to the second metal layer and the third metal layer, wherein the first microfluidic channel exposes two of the second bridge patterns.

3. The semiconductor chip with embedded microfluidic channels according to claim 2, wherein the third metal layer includes a first signal trace and second a second signal trace, the first signal trace is electrically independent from the second signal trace, and are electrically and respectively connected to the two of the second bridge patterns.

4. The semiconductor chip with embedded microfluidic channels according to claim 1, further comprising:
- a heater, embedded in the circuit structure layer, and suitable for heating the first microfluidic channel.

5. The semiconductor chip with embedded microfluidic channels according to claim 4, wherein a material of the heater includes polysilicon.

6. The semiconductor chip with embedded microfluidic channels according to claim 1, further comprising:
- a second microfluidic channel, embedded in the circuit structure layer, and disposed above the first microfluidic channel, wherein the first insulation layer has a plurality of micro via holes, and the second microfluidic channel is connected to the first microfluidic channel through the micro via holes.

7. The semiconductor chip with embedded microfluidic channels according to claim 6, a second height of the second microfluidic channel along the stacking direction is equal to a second thickness of the second metal layer along the stacking direction.

8. The semiconductor chip with embedded microfluidic channels according to claim 1, wherein the micro via hole includes a first portion and a second portion connected to each other along the stacking direction, a first width of the first portion along a direction perpendicular to the stacking direction is different from a second width of the second portion along the direction perpendicular to the stacking direction.

* * * * *